US008648214B2

(12) United States Patent  (10) Patent No.: US 8,648,214 B2
Gore et al.  (45) Date of Patent: Feb. 11, 2014

(54) PROCESSES SUITABLE FOR THE PREPARATION OF SALMETEROL

(75) Inventors: Vinayak G. Gore, Maharashtra (IN); Avinash C. Gaikwad, Maharashtra (IN); Maheshkumar Gadakar, Maharashtra (IN); Vinay Kumar Shukla, Maharashtra (IN)

(73) Assignee: Generics [UK] Limited (GB)

( * ) Notice: Subject to any disclaimer, the term of this patent is extended or adjusted under 35 U.S.C. 154(b) by 343 days.

(21) Appl. No.: 12/103,999

(22) Filed: Apr. 16, 2008

(65) Prior Publication Data

US 2008/0262267 A1  Oct. 23, 2008

Related U.S. Application Data

(63) Continuation of application No. PCT/GB2006/003857, filed on Oct. 17, 2006.

(30) Foreign Application Priority Data

Oct. 17, 2005 (IN) .......................... 1298/MUM/2005
May 31, 2006 (IN) ........................... 827/MUM/2006

(51) Int. Cl.
  *C07C 211/00* (2006.01)
(52) U.S. Cl.
  USPC ....................................... 564/336
(58) Field of Classification Search
  None
  See application file for complete search history.

(56) References Cited

U.S. PATENT DOCUMENTS

| | | | | |
|---|---|---|---|---|
| 3,468,881 | A * | 9/1969 | Szmuszkovicz | 540/484 |
| 4,952,729 | A | 8/1990 | Babad et al. | |
| 4,992,474 | A | 2/1991 | Skidmore et al. | |
| 5,011,993 | A | 4/1991 | Babad et al. | |
| 6,441,165 | B2 * | 8/2002 | Blanchard et al. | 540/549 |
| 6,620,977 | B1 * | 9/2003 | Hirata et al. | 568/648 |
| 6,911,560 | B2 * | 6/2005 | Procopiou | 564/346 |
| 2004/0152720 | A1 | 8/2004 | Hartig et al. | |
| 2005/0113608 | A1 | 5/2005 | Meyer et al. | |

FOREIGN PATENT DOCUMENTS

| | | |
|---|---|---|
| DE | 3414752 A1 | 10/1984 |
| EP | 0 422 889 A2 | 10/1990 |
| EP | 0422889 | 4/1991 |
| EP | 1132373 | 9/2001 |
| GB | 2140800 A | 12/1984 |
| GB | 2176476 | 12/1986 |
| JP | 03-133946 | 3/1991 |
| JP | 06-087800 | 6/1994 |
| JP | 11012219 | 1/1999 |
| JP | 2001247517 | 9/2001 |
| JP | 2002-525349 | 8/2002 |
| WO | WO 01/96278 A2 | 12/2001 |

OTHER PUBLICATIONS

Vippagunta et al. Advanced Drug Delivery Reviews 2001, 48, 3-26.*
Morissette et al. Advanced Drug Delivery Reviews 2004, 56, 275-300.*
Jasperse "Liquid/Liquid Separation: Extraction of Acids or Bases from Neutral Organics"; web.archive.org/web/20050507121610/ http://www.mnstate.edu/jasperse/Chem355/Acid-Base+Extraction.doc.pdf, published on the web May 7, 2005.*
Wayback machine print out providing evidence of publication date of the Jasperse article.*

(Continued)

*Primary Examiner* — Clinton Brooks
(74) *Attorney, Agent, or Firm* — Dorsey & Whitney LLP

(57) ABSTRACT

The present invention relates to processes for the preparation of 4-hydroxy-α'-[[[6-(4-phenylbutoxy)hexyl]amino]methyl]-1,3-benzenedimethanol 1-hydroxy-2-naphthoate (salmeterol xinafoate) (12a), the preparation of 4-hydroxy-α'-[[[6-(4-phenylbutoxy)hexyl]amino]methyl]-1,3-benzenedimethanol (salmeterol) (11), the preparation of protected N-[6-(4-phenylbutoxy)hexyl]amine intermediates (7), and the preparation of 6-substituted (4-phenylbutoxy) hexane intermediates (5), shown below, wherein X is a leaving group and Pg is a protecting group.

(5)

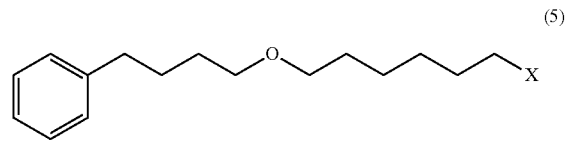

(7)

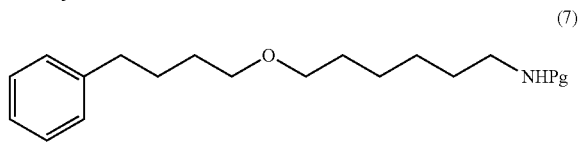

(11)

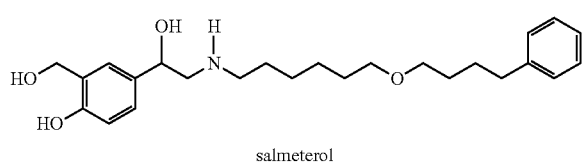

salmeterol (12a)

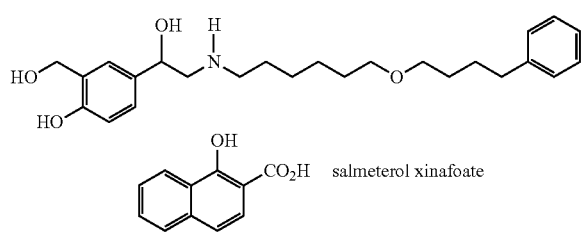

salmeterol xinafoate

52 Claims, 2 Drawing Sheets

(56) References Cited

OTHER PUBLICATIONS

Hett et al. "Enantioselective Synthesis of Salmeterol via Asymmetric Borane Reduction" Tetrahedron Letters 1994;35(50):9375-9378.
Nangia et al. "Synthesis of 1-amino-6-(4-phenyl-butoxy)hexane:Arylalkylamino group in Salmeterol" Indian Journal of Chemistry 1995:34B:629-631.

Rong et al. "A new Synthetic Approach to Salmeterol" Synthetic Communications, 1999;29(12):2155-2162.
Molinsky et al., "Improved synthesis of $^{13}$C, $^{2}$H$_3$- and $^{2}$H$_3$-salmetrol by Cs$_2$CO$_3$-mediated monoalkylation of a primary amine," *Journal of Labelled Compounds and Radiopharmaceuticals*, 2002, vol. 45, pp. 755-762.

\* cited by examiner

PROCESSES SUITABLE FOR THE PREPARATION OF SALMETEROL

CROSS-REFERENCE TO RELATED APPLICATION(S)

This application is a Continuation of International Patent Application PCT/GB2006/003857, filed on Oct. 17, 2006, which claims priority to India Application No. 1298/mum/2005, filed Oct. 17, 2005, and to India Application No. 827/mum/2006, filed May 31, 2006, the entire contents of which are hereby incorporated by reference.

FIELD OF THE INVENTION

The present invention relates to processes for the preparation of 4-hydroxy-α'-[[[6-(4-phenylbutoxy)hexyl]amino]methyl]-1,3-benzenedimethanol 1-hydroxy-2-naphthoate (salmeterol xinafoate) (12a), the preparation of 4-hydroxy-α'-[[[6-(4-phenylbutoxy)hexyl]amino]methyl]-1,3-benzenedimethanol (salmeterol) (11), the preparation of protected N-[6-(4-phenylbutoxy)hexyl]amine intermediates (7), and the preparation of 6-substituted (4-phenylbutoxy)hexane intermediates (5), shown below, wherein X is a leaving group and Pg is a protecting group.

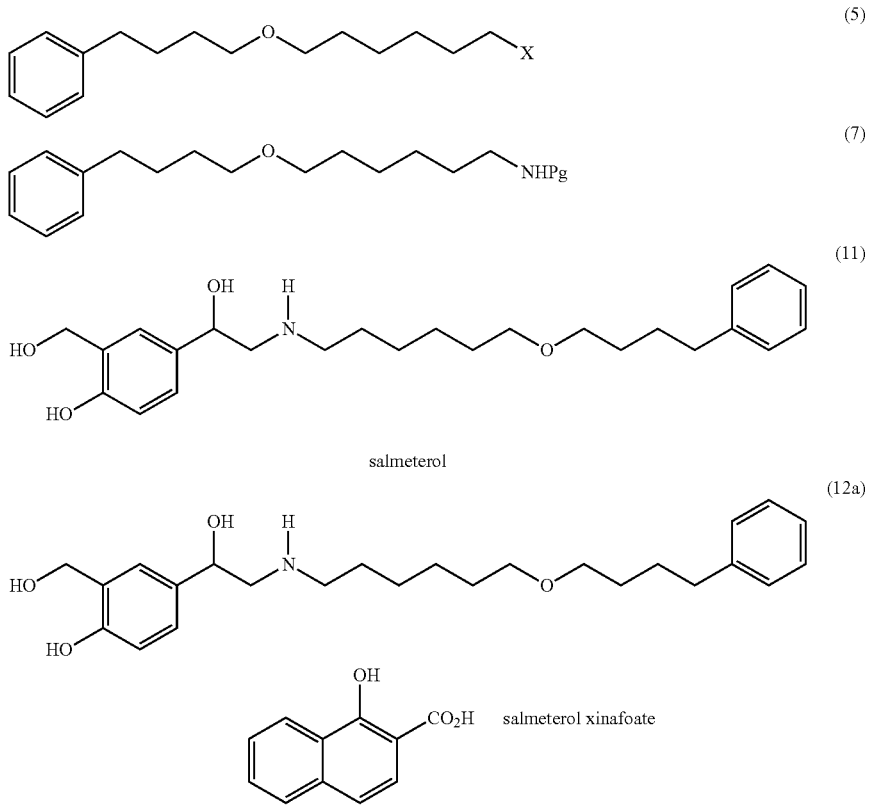

BACKGROUND OF THE INVENTION

The chemical species, 4-hydroxy-α'-[[[6-(4-phenylbutoxy)hexyl]amino]methyl]-1,3-benzenedimethanol is generically known as salmeterol.

Salmeterol and its pharmaceutically acceptable salts are long-acting beta-agonists. Salmeterol xinafoate, represented above, is a selective β2-adrenoreceptor agonist. It is clinically used as long-acting inhaled bronchodilator for maintenance treatment of asthma and to control nocturnal asthma. Unlike other bronchodilator drugs, salmeterol is more lipophilic and has many unusual pharmacological properties. The dosage strength is very small (0.021 mg as a metered dose and 0.046 mg as a dry powder inhaler). Due to its very small dosage strength, it is of utmost importance to have the highest possible purity of the API. Also many times the method of particle size reduction is very sensitive to the impurities present and therefore demands highest purity of the API in order to have consistent and desirable results.

There are several processes disclosed in the literature for the synthesis of salmeterol xinafoate, but all of them suffer severe disadvantages with respect to quality, especially on higher scale or on commercial manufacturing scale.

In all the reported synthetic schemes, N-[6-(4-phenylbutoxy)hexyl]benzenemethanamine (7a) serves as the key intermediate in the synthesis of salmeterol (GB Patent 2,176,476; U.S. Pat. No. 4,992,474; Tetrahedron Letters, vol. 35(50), pages 9375-9378, 1994; Synthetic Communications, vol. 29(12a), pages 2155-2162, 1999; and Indian Journal of Chemistry, vol. 34B, pages 629-631, 1995).

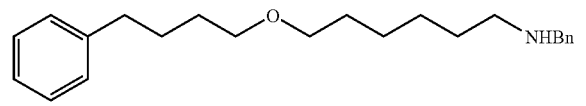

It is well known in the art that, when salmeterol is synthesised via intermediate (7a), the purity of the drug substance salmeterol is controlled by the purity of intermediate (7a) and to get the desired purity (more than 99.5%) of salmeterol, it is necessary to have the intermediate (7a) of purity of more than 99.5%.

The literature processes do not furnish intermediate (7a) in the required purity, unless methods like high vacuum distillation or purification by column chromatography are resorted to, which are not suitable for commercial manufacturing processes for obvious reasons.

Salmeterol, its salts and solvates are disclosed in GB Patent 2,176,476, which relates to phenethanolamine derivatives, to processes for their preparation, to pharmaceutical compositions comprising them, and to uses of these compounds as medicine.

Processes for the preparation of salmeterol intermediates and related derivatives are disclosed in GB Patent 2,176,476, U.S. Pat. No. 4,992,474 and Tetrahedron Letters, vol. 35(50), pages 9375-9378, 1994.

The present invention discloses a chemical method for purification of intermediate (7a) via formation of an acid salt (8). This method affords intermediate (7a) of very high purity (more than 99.5%).

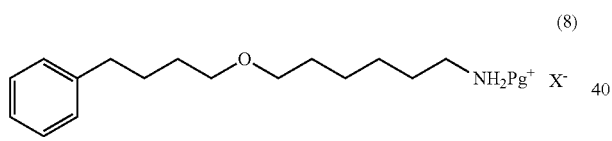

(8)

US 2005/0113608 uses KOH as a base and phase transfer (tetrabutyl ammonium hydrogen sulfate) as a catalyst in toluene as a solvent. The product is isolated after high vacuum distillation.

A preferred embodiment of the present invention uses NaH (sodium hydride) as a base, and Bu₄NBr (tetrabutyl ammonium bromide) as a catalyst. In addition to this catalyst the present invention uses NaI (sodium iodide), which helps to minimize side reactions and to get a cleaner product. The product need not be distilled, but can be taken up as such for the preparation of the key intermediate (7a) for salmeterol.

The key intermediate (7a) for salmeterol is disclosed the present application, which teaches a process with novel features viz. purification without vacuum distillation or chromatographic purification, and formation of acid salt (8) in an aqueous organic system.

The process disclosed in GB patent 2,176,476 uses tetrahydrofuran as a solvent with NaH and with catalyst tetrabutyl ammonium hydrogen sulfate. The product is purified by chromatographic purification.

The present inventors have further established that having the intermediate (7a) of highest purity may not be enough to get the desired quality of salmeterol because of the thermal instability of the subsequent intermediates.

Intermediate (9a) is isolated after stripping off the solvent (typically ethyl methyl ketone, acetone, ethyl acetate etc). It was observed that the intermediate (9a) decomposes even when the solvent is stripped off at 30° C. The impurities formed complicate subsequent reactions and inferior quality material is obtained. It is possible to control the decomposition in small-scale laboratory experiments, from which only milligram or a few gram quantities of salmeterol can be obtained. But on a commercial scale the decomposition is unavoidable. In fact, decomposition was observed even at 30° C. over a period of time. Similarly, the next sodium borohydride reduction step gave varied amounts of unknown impurities, which were difficult to separate to the required levels (less than 0.10%).

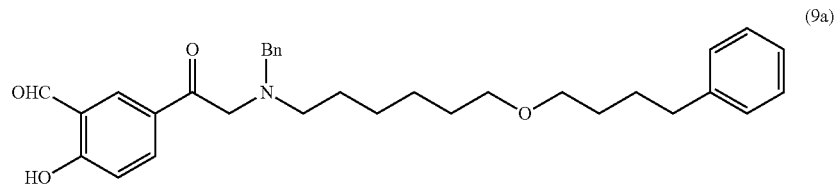 [SMILES: O=Cc1cc(C(=O)CN(CCCCCCOCCCCc2ccccc2)Cc2ccccc2)ccc1O]

(9a)

Thus the processes reported in the prior art suffer the following drawbacks:

(1) Use of either high vacuum distillation or column chromatography purification for N-[6-(4-phenylbutoxy)hexyl]benzenemethanamine (7a).

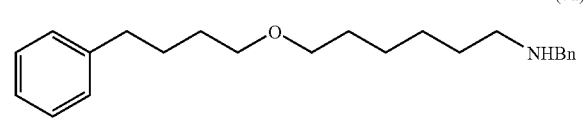

(7a)

(2) In the preparation of 2-hydroxy-5-[[[6-(4-phenylbutoxy)hexylbenzyl]amino]acetyl]benzaldehyde (9a), addition of the intermediate (7a) to intermediate (2a) generates impurities which are difficult to remove. In addition to that, after the reaction is over, the reaction mass is extracted in ethyl acetate. This extraction brings many impurities and resinous material with the product, which creates problems for the purification and isolation of the further intermediates. As per the prior art, this intermediate (9a) is isolated by distillation of the solvent, which again generates the impurities/resinous material. These impurities cannot be easily removed by chemical treatment or by conventional ways except column chromatography. Further, intermediate (9a) is thermally less stable and needs to be processed immediately for further steps.

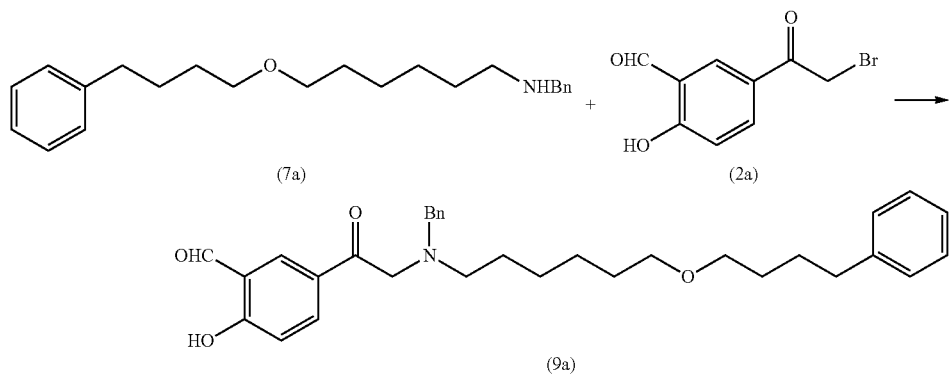

(3) The quantity of sodium borohydride used in the prior art processes is not sufficient for complete reduction. As sodium borohydride also reacts with methanol, this leaves some partially reduced products and also unreacted intermediate (9a) during the reaction. In order to push these partially reduced intermediates to the intermediate (10a) in the subsequent catalytic hydrogenolysis (N-debenzylation), the reaction needs to be prolonged.

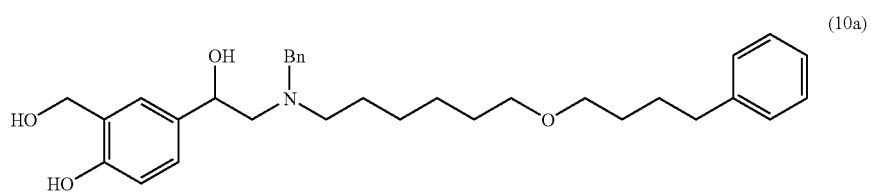 [SMILES: OCc1cc(C(O)CN(CCCCCCOCCCCc2ccccc2)Cc2ccccc2)ccc1O]

This leads to generation of impurity G (mentioned in the European Pharmacopoeia 5.2) and other unknown impurities above acceptable limits. These impurities are difficult to remove subsequently.

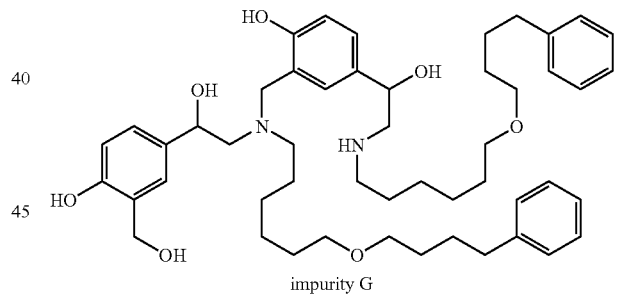

impurity G (4) In the preparation of 4-hydroxy-α'-[[[6-(4-phenylbutoxy)hexyl]amino]methyl]-1,3-benzenedimethanol (11) (i.e. salmeterol), because of the various impurities and resinous material formed in the earlier steps, the isolation of salmeterol (11) is difficult and tricky. Also, the quality varies from batch to batch, as there is very little control over the content of these impurities in the earlier steps.

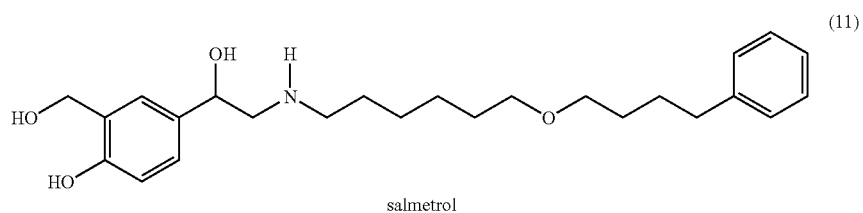

salmetrol

Because of these limitations the prior art processes are not suitable for scaling up and do not afford quality product.

The present inventors have circumvented the difficulties associated with the earlier processes to obtain salmeterol (11) consistently in very high purity. The process of the present invention is robust and reproducible and can be conveniently employed for commercial production.

OBJECTS OF THE INVENTION

It is an object of the present invention to provide a process for the preparation of highly pure salmeterol xinafoate, i.e. 4-hydroxy-α'-[[[6-(4-phenylbutoxy)hexyl]amino]methyl]-1,3-benzenedimethanol 1-hydroxy-2-naphthoate (12a).

It is another object of the present invention to provide a process for the preparation of highly pure salmeterol, i.e. 4-hydroxy-α'-[[[6-(4-phenylbutoxy)hexyl]amino]ethyl]-1,3-benzenedimethanol (11).

It is a further object of the present invention to eliminate cumbersome purification techniques like high vacuum fractional distillation or chromatographic purification.

It is yet another object of the present invention to develop a scalable process, which addresses the issue of thermal instability.

Thus the present invention provides a process for the preparation of highly pure salmeterol xinafoate, comprising the steps of:
(i) reacting intermediate (2a) and intermediate (7a) in an organic solvent by adding a solution of intermediate (2a) into a solution of intermediate (7a) at 0-5° C. to give intermediate (9a);
(ii) isolating intermediate (9a) selectively in an organic non-polar solvent;
(iii) reducing intermediate (9a) in an organic biphasic solvent system in the presence of a large excess of sodium borohydride to give intermediate (10a);
(iv) debenzylating intermediate (10a) at ambient pressure to give salmeterol (11); and
(v) adding xinafoic acid to crystallize the xinafoate salt of salmeterol (12a).

It is yet another object of the present invention to provide:
(i) pure salmeterol salts (12), in particular pure salmeterol xinafoate (12a);

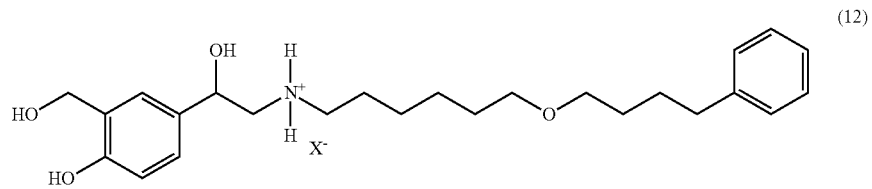

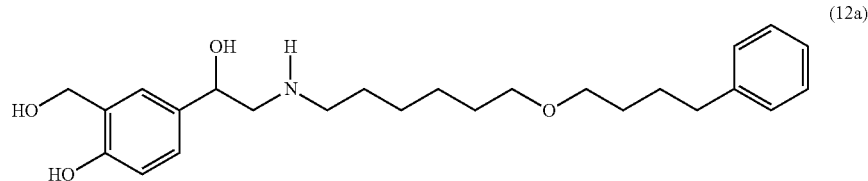

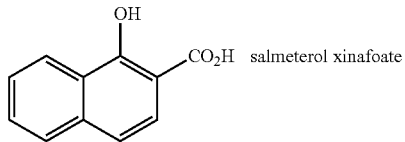

(ii) pure salmeterol (11);

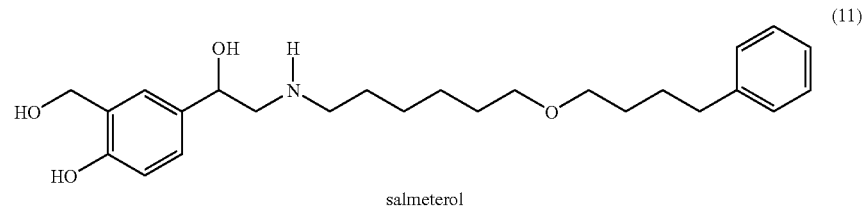 [SMILES: OCc1cc(C(O)CNCCCCCCOCCCCc2ccccc2)ccc1O ; "salmeterol"]

(iii) pure protected N-[6-(4-phenylbutoxy)hexyl]amine intermediates (7), in particular pure benzenemethanamine (7a); and

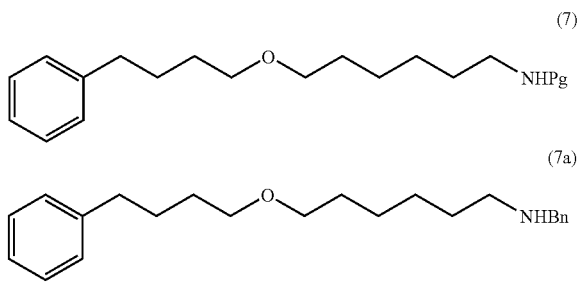

(iv) pure 6-substituted (4-phenylbutoxy)hexane intermediates (5), in particular pure bromoether intermediate (5a).

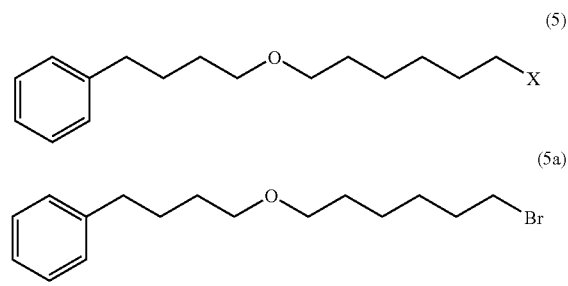

SUMMARY OF THE INVENTION

A first aspect of the present invention provides a process of preparing an ether (5), comprising the step of:
(a) reacting 4-phenyl-1-butanol (3) and X—(CH$_2$)$_6$—X (4) in the presence of a phase transfer agent and NaI to obtain ether (5), wherein X are independently leaving groups.

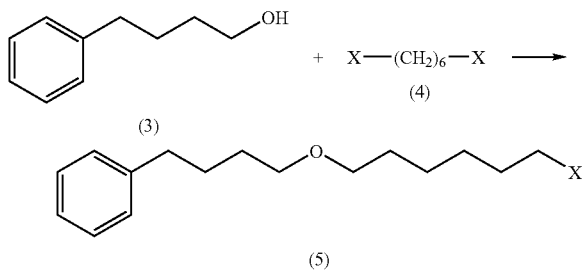

X are independently leaving groups. Preferably, X are independently —Cl, —Br, —I, —OTs (tosylate), —OMs (mesylate) or —OTf (triflate). Most preferably, X—(CH$_2$)$_6$—X (4) is Br—(CH$_2$)$_6$—Br (4a).

Preferably, the reaction of step (a) takes place in the presence of a base. If present, the base may be NaH, KH, NaOH, KOH, NaNH$_2$, NaOMe, KOtBu, nBuLi, 1,4-diazabicyclo[2,2,2]octane (DABCO), or 1,8-diazabicyclo[5,4,0]undec-7-ene (DBU). If present, the base is preferably NaH.

The phase transfer agent may be a quaternary ammonium or phosphonium salt, such as Bu$_4$NBr, Bu$_4$NHSO$_4$, C$_{16}$H$_{33}$N(CH$_3$)$_3$Cl, C$_{16}$H$_{33}$N(CH$_3$)$_3$Br, C$_{16}$H$_{33}$N(CH$_3$)$_3$HSO$_4$, n-butyl-pyridinium chloride, cetylpyridinium chloride, cetylpyridinium bromide, 1-butyl-1-methyl-pyrrolidinium chloride, C$_{16}$H$_{33}$PBu$_3$Cl, and C$_{16}$H$_{33}$PBu$_3$Br. Preferably, the phase transfer agent is Bu$_4$NBr. Preferably, the phase transfer agent is present in a catalytic amount.

Preferably, the NaI is present in a catalytic amount.

Preferably, the reaction of step (a) is carried out in an aprotic solvent. Typical aprotic solvents are toluene, dimethylformamide, dimethyl sulfoxide, tetrahydrofuran, xylene, methyl t-butyl ether, diisopropyl ether, and mixtures thereof. A preferred aprotic solvent is toluene.

A second aspect of the present invention provides a process of preparing an amine (7) or a salt thereof, comprising the steps of:
(a) carrying out step (a) of the first aspect of the present invention, and
(b) reacting ether (5) and protected amine PgNH$_2$ (6) in the presence of a base to obtain amine (7) or a salt thereof, wherein Pg is a protecting group.

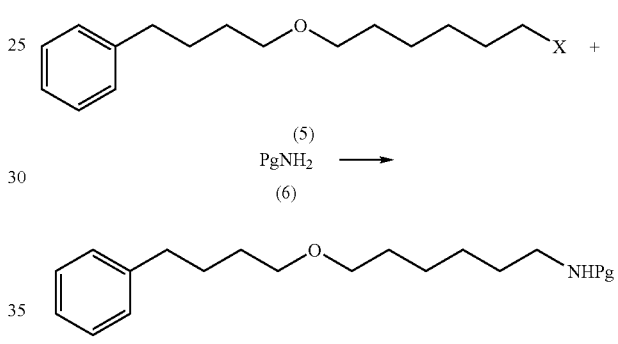

Suitable protecting groups Pg are known in the art, for example from chapter 7 of "Protective Groups in Organic Synthesis" by T. W. Greene and P. G. M. Wuts (Wiley-Interscience, 2$^{nd}$ edition, 1991), which is enclosed herein by reference. For example, protected amine PgNH$_2$ (6) used in step (b) may be benzylamine; benzylamine para- or ortho-substituted with an alkyl, alkoxy or halo group such as -Me, -Et, —OMe, —OEt, —Cl and —Br; or alkoxycarbonyl-amine such as benzyloxycarbonyl-amine, t-butoxycarbonyl-amine, 2-(4-biphenylyl)-isopropoxycarbonyl-amine or 9-fluorenylmethoxycarbonyl-amine. Preferably, protected amine PgNH$_2$ (6) used in step (b) is benzylamine.

Preferably, the base used in step (b) comprises triethylamine, potassium carbonate, sodium carbonate, pyridine, pyrrolidine, piperidine, diisopropylamine or diisopropylethylamine. A preferred base is triethylamine.

Preferably, the reaction of step (b) is carried out in the presence NaI. If present, the NaI is preferably present in a catalytic amount.

Preferably, the reaction of step (b) is carried out in an organic solvent. Typical organic solvents are acetonitrile, tetrahydrofuran, dimethylformamide, dimethylacetamide, methanol, ethanol, n-propanol, isopropanol, toluene, xylene, and mixtures thereof. A preferred organic solvent is acetonitrile.

Preferably the process further comprises the steps of:

(c) converting amine (7) into a salt (8) thereof, wherein X is an anion,

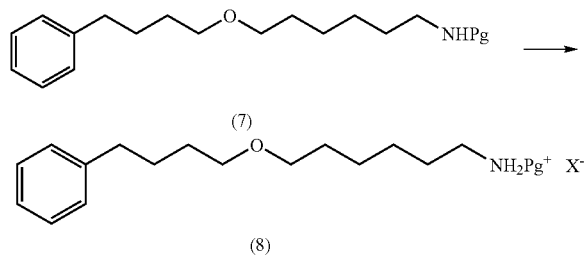

(d) purifying the salt (8), and
(e) converting the purified salt (8) back into amine (7).

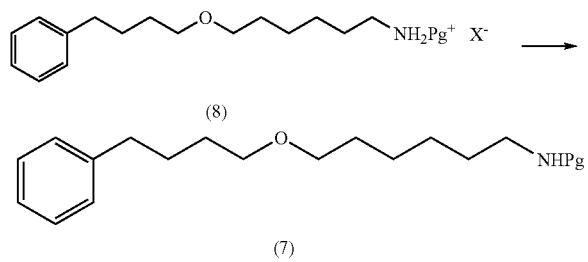

Preferably, the salt (8) is a hydrofluoride, hydrochloride, hydrobromide, hydroiodide, tartrate, formate, acetate, sulfate, hydrogen sulfate, nitrate, benzoate, maleate, fumarate, methanesulphonate, benzylsulfonate or citrate salt. More preferably, the salt (8) is a hydrochloride salt (8a).

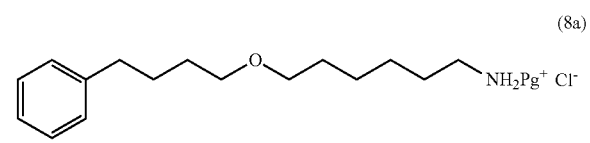

Preferably, the conversion step (c) is carried out in a non-polar halogenated solvent in the presence of water. Typical non-polar halogenated solvents are dichloromethane, dichloroethane, chloroform, and mixtures thereof. A preferred non-polar halogenated solvent is dichloromethane.

Preferably, the purification step (d) comprises washing the salt (8) with a non-polar solvent. Typical washing solvents are pentane, hexane, heptane, cyclohexane, diethyl ether, diisopropyl ether, t-butyl methyl ether, and mixtures thereof. A preferred washing solvent is n-heptane.

Alternatively or additionally, the purification step (d) comprises recrystallising the salt (8), preferably using a polar protic solvent and a non-polar aprotic solvent. Typical polar protic solvents are methanol, ethanol, isopropanol, and mixtures thereof. A preferred polar protic solvent is isopropanol. Typical non-polar aprotic solvents are pentane, hexane, heptane, toluene, and mixtures thereof. A preferred non-polar aprotic solvent is n-heptane. In a preferred embodiment, the purification step (d) comprises recrystallising the salt (8) using isopropanol and n-heptane.

Preferably, in step (e), the purified salt (8) is converted into amine (7) using a base, preferably an inorganic base such as $Na_2CO_3$, $NaHCO_3$, $K_2CO_3$, $Li_2CO_3$ or $Cs_2CO_3$. Preferably, the base used in step (e) is $Na_2CO_3$.

Preferably, the amine (7) or salt thereof is obtained from any of the processes of the second aspect of the present invention more than 90%, more than 95%, more than 98%, more than 99%, more than 99.5%, or more than 99.7% pure as measured by HPLC.

Preferably, the amine (7) or salt thereof is obtained in an overall yield of more than 50%, more than 60%, more than 70%, or more than 80% by weight from 4-phenyl-1-butanol (3).

The process of the present application is suitable for industrial scale manufacture of amine (7) or a salt thereof. Preferably, amine (7) or a salt thereof is obtained in batches of 100 g or more, 200 g or more, 500 g or more, 1 kg or more, 5 kg or more, or 10 kg or more.

Preferably, the processes of the first and second aspects of the present invention are carried out without purifying bromoether (5), amine (7) or salt (8) by chromatography or high vacuum fractional distillation, preferably not by any high vacuum distillation, preferably not by any distillation.

A third aspect of the present invention provides a process of preparing salmeterol (11) or a salt or solvate thereof, comprising the steps of:

(i) reacting an amine (7) and an aldehyde (2) to obtain aldehyde (9), wherein X is a leaving group and Pg is a protecting group,

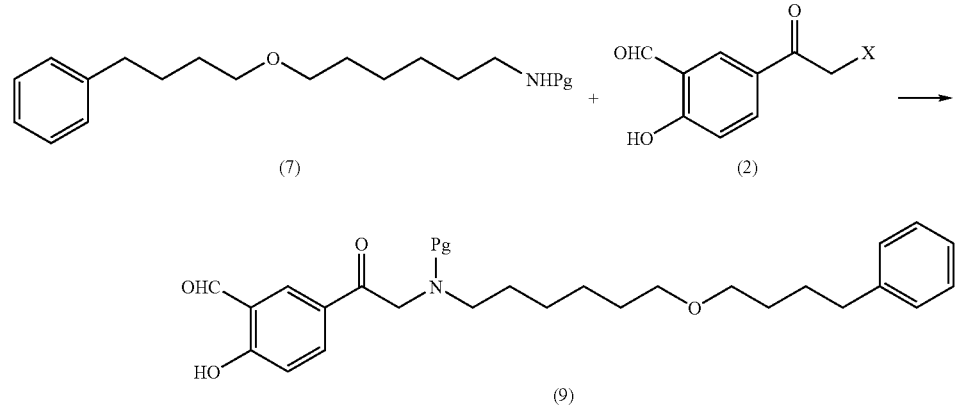

(ii) reducing aldehyde (9) to obtain alcohol (10), and

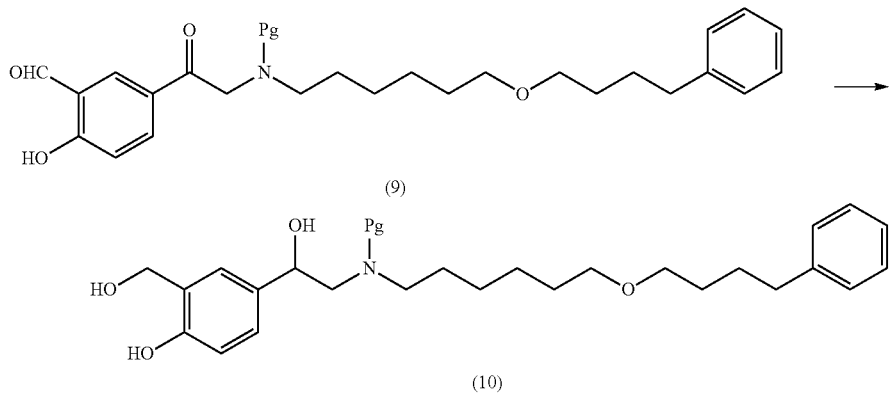

(iii) deprotecting alcohol (10) to obtain salmeterol (11).

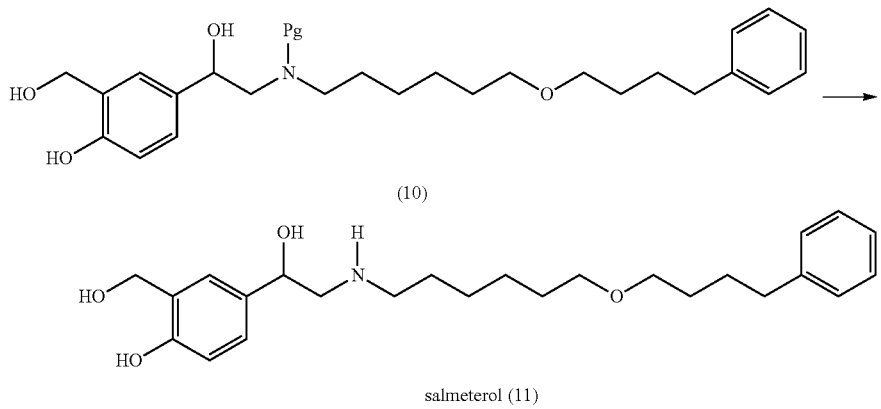

Salmeterol (11) can be used as API both, in its free base form and its acid addition salt form. For the purposes of this invention, a "salt" of salmeterol (11) is usually an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, xinafoic, propionic, butyric, glycolic, lactic, mandelic, citric, acetic, benzoic, 2- or 4-methoxy-benzoic, 2- or 4-hydroxy-benzoic, 2- or 4-chloro-benzoic, salicylic, succinic, malic or hydroxysuccinic, tartaric, fumaric, maleic, hydroxymaleic, oleic, glutaric, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid). A preferred salt is the xinafoic acid addition salt.

In addition to pharmaceutically acceptable acid addition salts, other acid addition salts are included in the present invention, since they have potential to serve as intermediates in the purification or preparation of other, for example, pharmaceutically acceptable, acid addition salts, or are useful for identification, characterisation or purification of the free base.

Additionally, for the purposes of this invention, a "salt" of salmeterol (11) can also be formed between a hydroxy functionality of salmeterol (11) and a suitable cation. Suitable cations include, but are not limited to, lithium, sodium, potassium, magnesium, calcium and ammonium. The salt may be a mono-, di- or tri-salt. Preferably the salt is a mono- or di-sodium salt. Preferably the salt is a pharmaceutically acceptable salt.

Preferably, step (i) is carried out in the presence of a base. Preferably, the base is an organic base such as triethylamine, tributylamine, diisopropylamine, diisopropylethylamine, pyridine, pyrrolidine, piperidine or morpholine. Preferably, the base is diisopropylethylamine.

Preferably, the reaction in step (i) is carried out in an organic solvent. Typical organic solvents are acetonitrile, methanol, ethanol, isopropanol, tetrahydrofuran, dimethylformamide, dimethyl sulfoxide, diethyl ether, diisopropyl ether, acetone, methyl ethyl ketone, and mixtures thereof. A preferred organic solvent is methyl ethyl ketone.

Preferably, in step (i), a solution of aldehyde (2) is added into a solution of amine (7).

Preferably, the reaction of step (i) is carried out at a temperature of 0-15° C., more preferably 0-10° C.

Preferably, in step (i), the product aldehyde (9) is not isolated, but extracted into a non-polar solvent. Typical extraction solvents are pentane, hexane, heptane, cyclohexane, diethyl ether, diisopropyl ether, t-butyl methyl ether, and mixtures thereof. A preferred extraction solvent is n-heptane. Preferably, the extracted solution comprising aldehyde (9) is used directly, i.e. without removal of the solvent, in step (ii).

The reduction of step (ii) may be carried out using a reducing agent such as $NaBH_4$, $NaCNBH_3$, $LiAlH_4$, $LiBH_4$ or $Zn(BH_4)_2$. Preferably, the reduction of step (ii) is carried out using $NaBH_4$. Preferably, an excess of $NaBH_4$ is used. Preferably, the aldehyde (9) and $NaBH_4$ are used in a ratio of 1:4-10, preferably in a ratio of 1:5-8, preferably in a ratio of about 1:7 of aldehyde (9): $NaBH_4$.

Preferably, the reduction of step (ii) is carried out in a biphasic solvent system. Preferably, the biphasic solvent system comprises a $C_{1-3}$ alcohol and a $C_{1-7}$ hydrocarbon. Typical $C_{1-3}$ alcohols are methanol, ethanol, isopropanol, and mixtures thereof. A preferred $C_{1-3}$ alcohol is methanol. Typical $C_{1-7}$ hydrocarbons are pentane, hexane, heptane, cyclohexane, and mixtures thereof. A preferred $C_{1-7}$ hydrocarbon is n-heptane.

In step (iii), depending on the protecting group Pg used, alcohol (10) may be deprotected by catalytic hydrogenolysis (using hydrogen over a catalyst) or chemical hydrogenolysis (using, for example, triethyl silane or trifluoroacetic acid). Preferably, alcohol (10) is deprotected by catalytic hydrogenolysis. Pd/C, Pt/C, Rh/C or Re/C may be used as the hydrogenation catalyst. Preferably, Pd/C is used as the hydrogenation catalyst, such as 10% Pd/C or 20% Pd/C. Preferably, the hydrogen gas is used at a pressure of 2-3 kg/cm².

Depending on the protecting group Pg used, the reduction of step (ii) and the deprotection of step (iii) may be carried out in the same reaction.

Preferably, amine (7) used in step (i) is prepared using a process of the second aspect of the present invention.

Following step (iii), the salmeterol (11) is preferably further converted into a salt thereof, such as the salts described above, for example, the xinafoate salt (12a).

Preferably, the salmeterol (11) or salt or solvate thereof is obtained more than 90%, more than 95%, more than 97%, more than 98%, more than 99%, or more than 99.5% pure as measured by HPLC.

Preferably, the salmeterol (11) or salt or solvate thereof is obtained in an overall yield of more than 12%, more than 15%, or more than 20% by weight from amine (7).

The process of the present application is suitable for industrial scale manufacture of salmeterol (11) or a salt or solvate thereof. Preferably, salmeterol (11) or a salt or solvate thereof is obtained in batches of 150 g or more, 250 g or more, 500 g or more, 1 kg or more, 5 kg or more, or 10 kg or more.

Preferably, the processes of the third aspect of the present invention are carried out without purifying aldehyde (9), alcohol (10), salmeterol (11) or salmeterol salt (12) by chromatography or high vacuum fractional distillation, preferably not by any high vacuum distillation, preferably not by any distillation.

A further aspect of the present invention provides an amine (7) or a salt thereof, prepared according to a process of the second aspect of the present invention, wherein Pg is a protecting group.

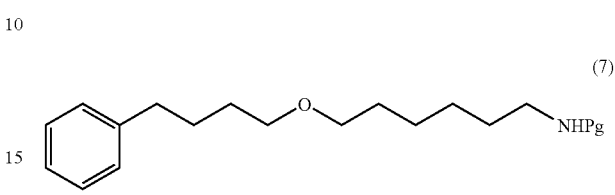

(7)

A further aspect of the present invention provides salmeterol (11) or a salt or solvate thereof, such as the xinafoate salt (12a), prepared according to a process of the third aspect of the present invention.

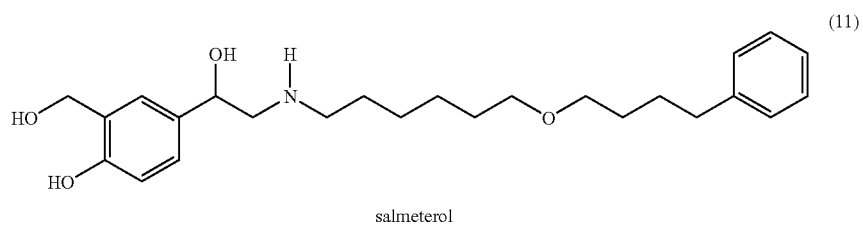 [SMILES: OCc1cc(C(O)CNCCCCCCOCCCCc2ccccc2)ccc1O]

salmeterol (11)

A further aspect of the present invention provides an amine (7) or a salt thereof, wherein Pg is a protecting group, and wherein the amine (7) or the salt thereof is more than 90% pure, preferably more than 95% pure, preferably more than 98% pure, preferably more than 99% pure, preferably more than 99.5% pure, and even more preferably more than 99.7% pure as measured by HPLC.

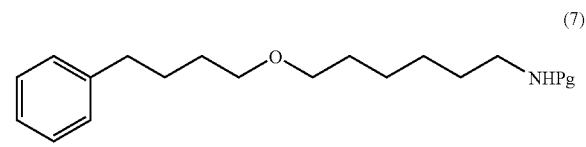

(7)

A further aspect of the present invention provides a salt (8), wherein Pg is a protecting group and X is an anion, and wherein the salt (8) is more than 90% pure, preferably more than 95% pure, preferably more than 98% pure, preferably more than 99% pure, preferably more than 99.5% pure, and even more preferably more than 99.7% pure as measured by HPLC.

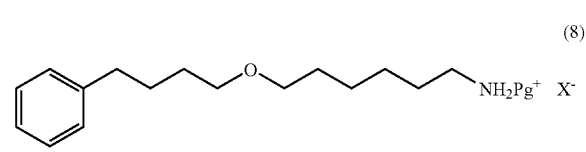

(8)

A further aspect of the present invention provides salmeterol (11) or a salt or solvate thereof, wherein the salmeterol (11) or the salt or solvate thereof is more than 95% pure, preferably more than 97% pure, preferably more than 98% pure, preferably more than 99% pure, and even more preferably more than 99.5% pure as measured by HPLC.

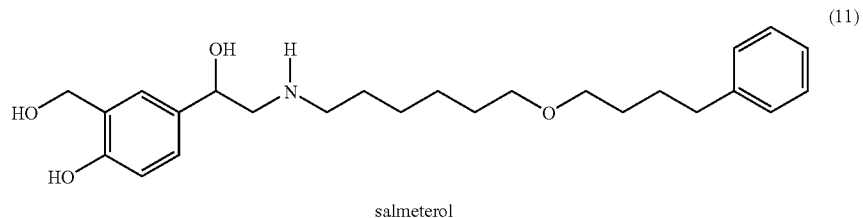 [SMILES: OCc1cc(C(O)CNCCCCCCOCCCCc2ccccc2)ccc1O]

salmeterol

A further aspect of the present invention provides salmeterol xinafoate salt (12a), wherein the salmeterol xinafoate salt (12a) is more than 95% pure, preferably more than 97% pure, preferably more than 98% pure, preferably more than 99% pure, and even more preferably more than 99.5% pure as measured by HPLC.

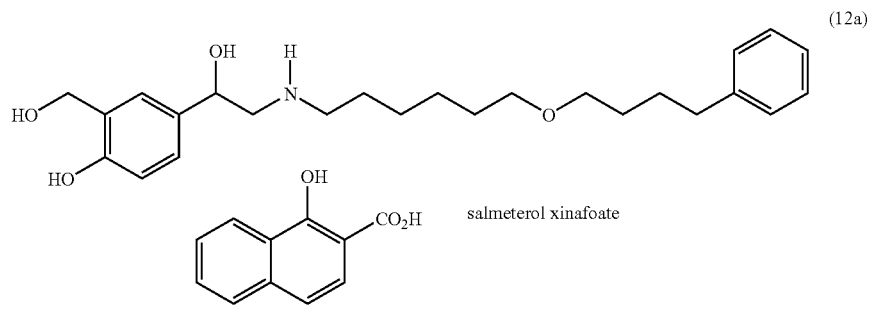 [SMILES: OCc1cc(C(O)CNCCCCCCOCCCCc2ccccc2)ccc1O ; O=C(O)c1ccc2ccccc2c1O]

salmeterol xinafoate

A further aspect of the present invention provides salmeterol (11) or a salt or solvate thereof, comprising less than 0.1% of impurity G.

A further aspect of the present invention provides salmeterol xinafoate salt (12a), comprising less than 0.1% of impurity G.

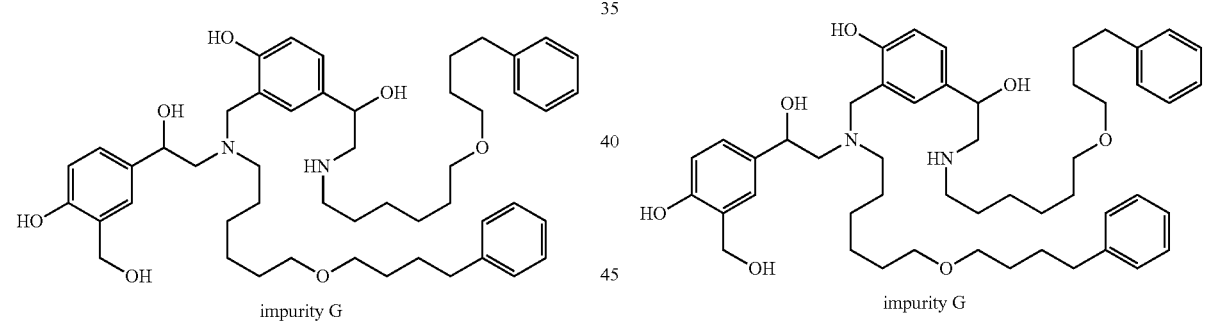

impurity G impurity G

A further aspect of the present invention provides salmeterol (11) or a salt or solvate thereof, comprising less than 0.2% of impurity D.

A further aspect of the present invention provides salmeterol xinafoate salt (12a), comprising less than 0.2% of impurity D.

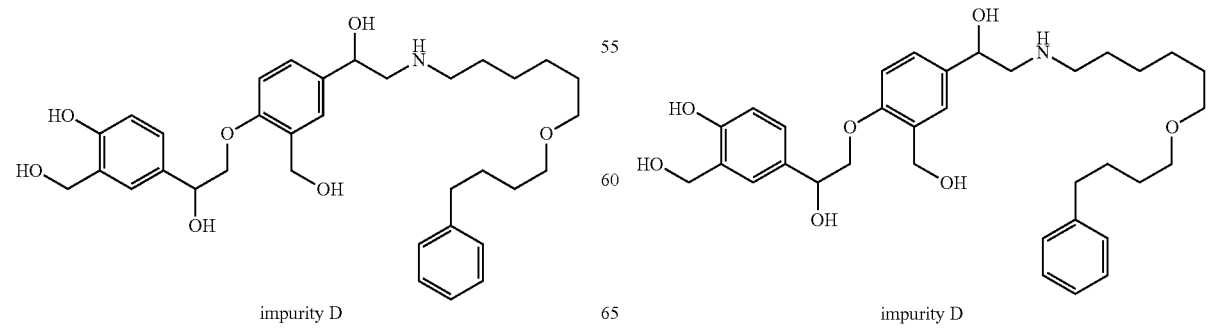

impurity D impurity D

The amounts of impurities G and D contained in salmeterol (11) or salmeterol xinafoate salt (12a) can be measured as set out in the European Pharmacopoeia 5.2.

BRIEF DESCRIPTION OF THE DRAWINGS

The present invention will now be described by way of example with reference to the accompanying drawings in which.

DETAILED DESCRIPTION

Figure 1:
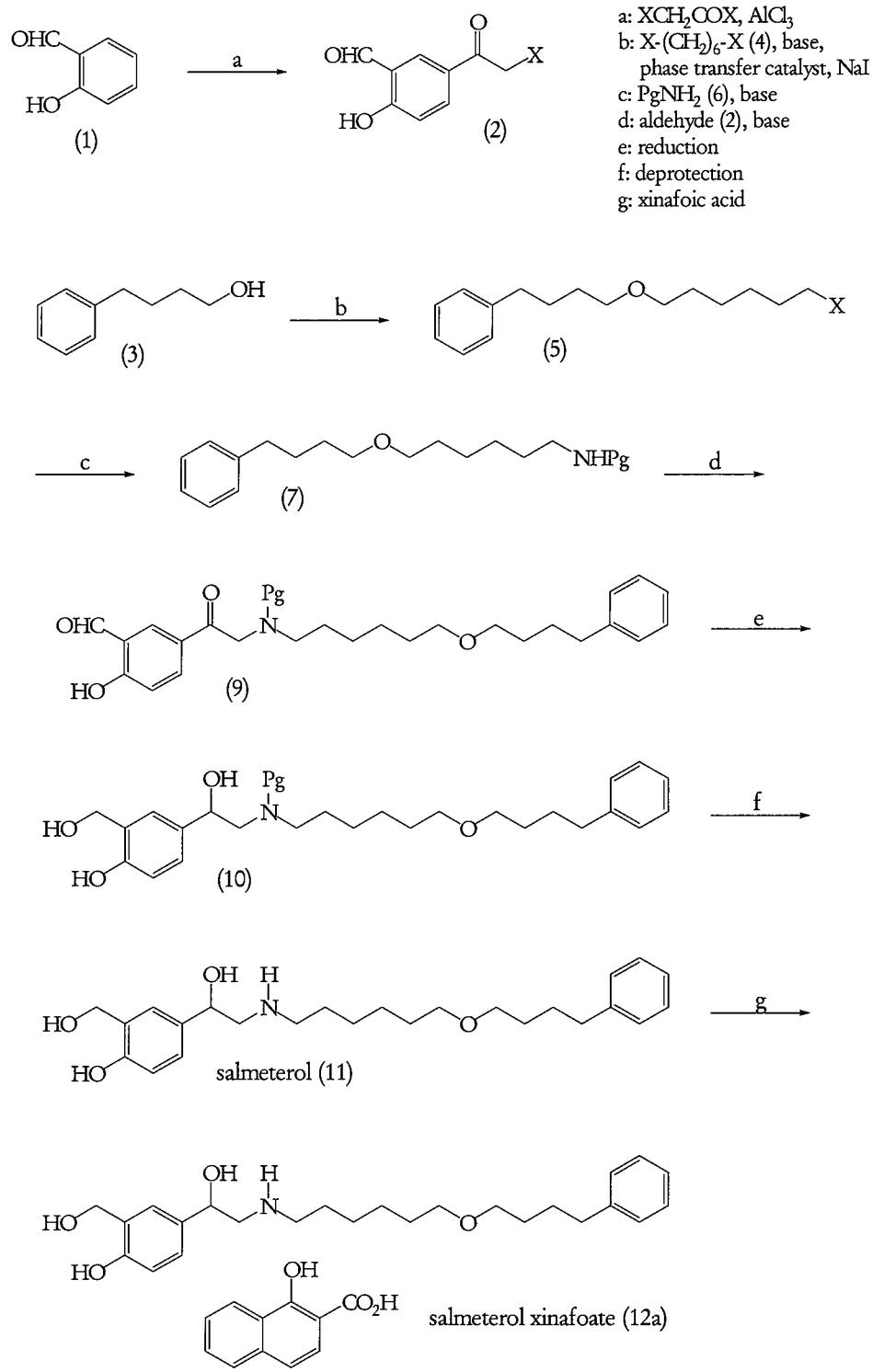
FIG. 1 shows a general reaction scheme in accordance with the present invention.
Figure 2:
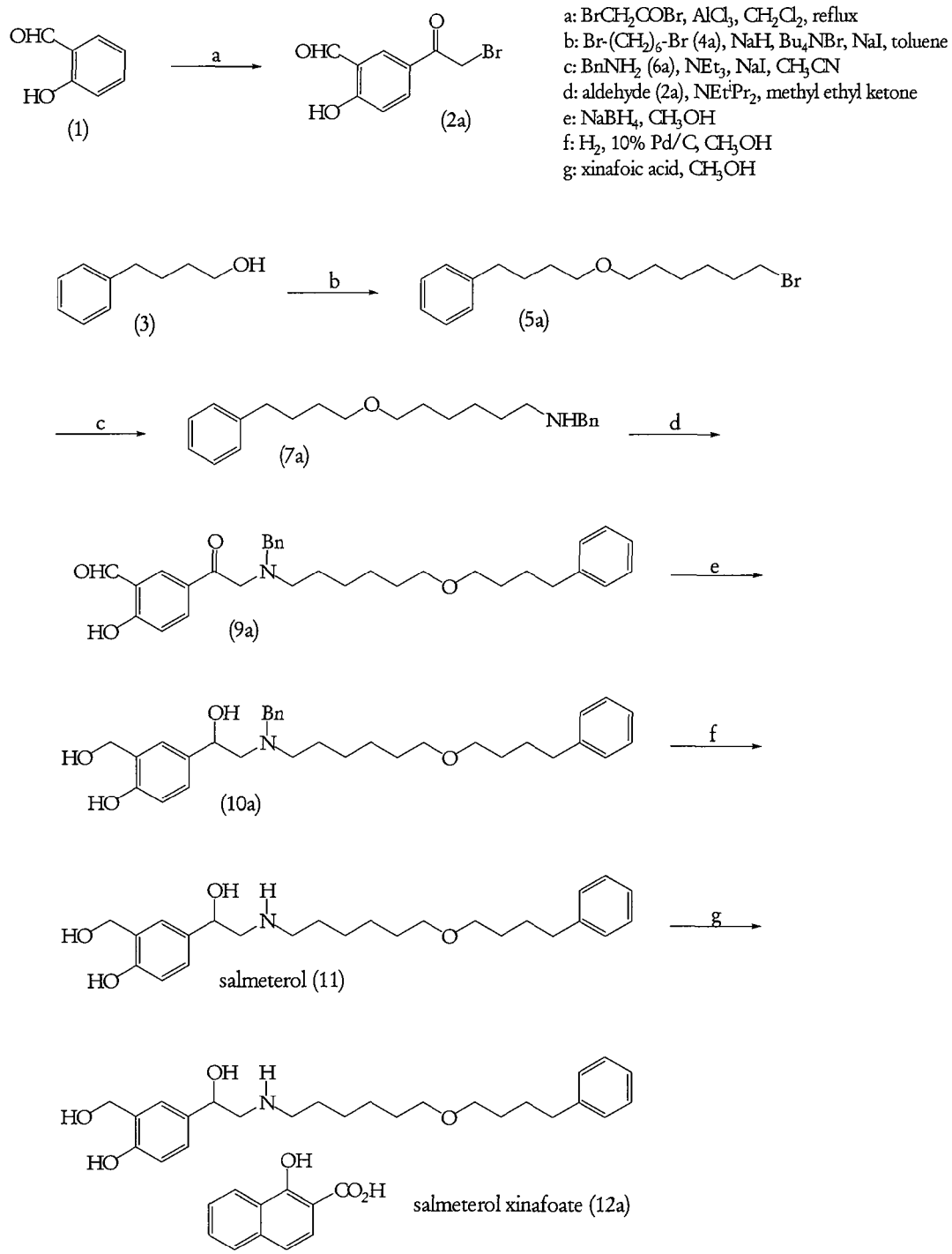
FIG. 2 shows a preferred reaction scheme in accordance with the present invention.

The present inventors have addressed the need for a process, which yields salmeterol xinafoate (12a) with very high HPLC purity (more than 99.5%) consistently.

In preferred embodiments the process of the present invention makes use of a chemical purification to achieve a very high purity of the key intermediate (7), a selective addition sequence for the preparation of intermediate (9), a novel biphasic organic solvent system for the selective reduction and isolation of intermediate (10), and a controlled reduction of intermediate (10) to obtain salmeterol (11) (see Scheme 1).

(a) Following the procedure described in the literature (Synthetic Communications, vol. 29(12a), pages 2155-2162, 1999; U.S. Pat. No. 5,011,993; and U.S. Pat. No. 4,952, 729), intermediate (2a) was synthesized using 2-hydroxybenzaldehyde (1) and bromoacetyl bromide. Intermediate (2a) thus obtained was purified by washing with n-heptane to yield the intermediate with more than 98% HPLC purity.

(b) Crude intermediate N-[6-(4-phenylbutoxy)hexyl]benzenemethanamine (7a) was obtained by reacting bromoether intermediate (5a) with benzylamine (6a) in organic solvents like acetonitrile, tetrahydrofuran, dimethylformamide, dimethylacetamide, methanol, ethanol, n-propanol, isopropanol, toluene or xylene (preferably acetonitrile), in the presence of a base like triethylamine, potassium carbonate, sodium carbonate, pyridine, pyrrolidine, piperidine, diisopropylamine or diisopropylethylamine (preferably triethylamine).

(c) Intermediate (7a) was converted into the corresponding acid salt (8) such as hydrochloride, hydrobromide, hydroiodide, acetate, sulfate or hydrogen sulfate salt (preferably hydrochloride salt), which was isolated by adding non-polar solvents like heptane, hexane or pentane, or ethereal solvents like diethyl ether or diisopropyl ether (preferably heptane).

(d) N-[6-(4-Phenylbutoxy)hexyl]benzenemethanamine hydrochloride (8b) was purified by crystallizing from isopropanol and n-heptane to obtain HPLC purity of more than 99.5%.

(e) The free base was liberated from the corresponding N-[6-(4-phenylbutoxy)hexyl]benzenemethanamine hydrochloride (8b) with HPLC purity of more than 99.5%, suitable for the preparation of salmeterol xinafoate (12a) with very high HPLC purity.

(f) Intermediate (2a) was reacted with intermediate (7a) in solvents like acetonitrile, lower aliphatic alcohols, tetrahydrofuran, dimethylformamide, dimethyl sulfoxide, diethyl ether or diisopropyl ether, and ketonic solvents like acetone or methyl ethyl ketone (preferably methyl ethyl ketone). The reaction was performed by adding a solution of intermediate (2a) into a solution of intermediate (7a) at 0-5° C. The prior art sequence of addition, where a solution of intermediate (7a) was added into a solution of intermediate (2a) gave inferior quality intermediate (9a) containing a lot of unknown impurities.

(g) Intermediate (9a) was isolated selectively in organic solvents like n-heptane, hexane, pentane, cyclohexane, diisopropyl ether or t-butyl methyl ether (preferably n-heptane), after quenching the reaction with water to avoid the decomposition and resinous material formation. The solvent was not stripped off as in the prior art work up, but intermediate (9a) was simply extracted in n-heptane at 20-30° C.

(h) The carbonyl groups in intermediate (9a) were reduced in an organic biphasic solvent system involving typically lower aliphatic alcohols viz. methanol, ethanol or isopropanol, and $C_{1-7}$ hydrocarbons viz. pentane, hexane or heptane (preferably methanol and n-heptane), in the presence of a large excess of sodium borohydride at ambient temperature. The immiscible non-polar solvent, e.g. n-heptane, helps in removing the unreacted intermediate (9a), the partially reduced product and non-polar impurities selectively which can be easily separated after the reaction is over. When stoichiometric quantities or slightly excess quantities of sodium borohydride were used, the reduction of the benzylic carbonyl was not complete and this resulted in formation of unknown impurities in the subsequent hydrogenation step. Therefore, it was necessary to have a clean and complete reduction of both carbonyl groups to the corresponding alcohol.

(i) Intermediate (10a) was isolated from the methanol layer by quenching with aqueous HCl solution to break the boron complex and then extracting with ethyl acetate after adjusting the pH to 8-9.

(j) Intermediate (10a) was subjected to hydrogenolysis (debenzylated) in a controlled way in methanol at ambient temperature using 20% palladium on charcoal with strict control on the formation of impurity G (European Pharmacopoeia 5.2) with online HPLC monitoring. It was observed that the duration of the hydrogenation reaction influenced the formation of impurities D and G (European Pharmacopoeia 5.2). The best control was obtained when the hydrogen gas was purged between 2-3 kg/cm². It was observed that higher pressure resulted in formation of impurity G in higher proportion, whereas pressure lower than 2-3 kg/cm² led to higher proportion of impurity D.

(k) The xinafoate salt (12a) of salmeterol was formed by treating purified salmeterol (11) with xinafoic acid (i.e. 1-hydroxy-2-naphthoic acid) followed by purification from methanol.

Details of the invention, its objects and advantages are explained hereunder in greater detail in relation to non-limiting exemplary illustrations.

EXAMPLES

Example 1

Preparation of
5-(Bromoacetyl)-2-hydroxybenzaldehyde (2a)

(Synthetic Communications, vol. 29(12a), pages 2155-2162, 1999; and U.S. Pat. No. 5,011,993)

To a suspension of aluminium chloride (4 m/m) in dichloromethane (10 volumes), was added slowly bromoacetyl bromide (1.2 m/m) at 10° C. and then the temperature was brought to 30° C. The reaction mass was stirred at this temperature for an hour and to this was added a solution of 2-hydroxybenzaldehyde (1) in dichloromethane at 30° C. The reaction mixture was stirred at 35-40° C. for 12-15 hours and then quenched in water at 0-5° C. The dichloromethane layer was separated and distilled off. To the slurry obtained, n-heptane was added and stirred for 15 minutes. This slurry was then filtered and the wet cake was washed with n-heptane (2 volumes). The wet cake was dried at 50° C. to constant weight to obtain intermediate (2a).

Yield: 55% w/w
HPLC purity: 97-99%

Example 2

Preparation of Bromoether (5a)

To a suspension of sodium hydride (0.9 m/m) in toluene, 4-phenyl-1-butanol (3) (1.0 m/m) was added at 25-30° C. followed by addition of 1,6-dibromohexane (4a) (1.2 m/m), sodium iodide and tetrabutyl ammonium bromide in catalytic amounts. The reaction mixture was stirred at 45-50° C. under a nitrogen gas atmosphere for 15-20 hours. The reaction mixture was quenched with water. The toluene layer was washed by water and the solvent was distilled off under reduced pressure to obtain a light yellow coloured liquid. The crude product bromoether (5a) thus obtained was used as such for the preparation of N-[6-(4-phenylbutoxy)hexyl]benzenemethanamine as described below.

Example 3

Preparation of N-[6-(4-phenylbutoxy)hexyl]benzenemethanamine hydrochloride (8b)

A mixture of benzylamine (6a) (3 m/m), triethylamine (2 m/m), and sodium iodide in catalytic amount in acetonitrile was heated to 45-50° C. under stirring. To this, bromoether (5a) was added slowly at the said temperature and the reaction was continued until TLC monitoring showed disappearance of bromoether intermediate (5a). Then solvent, excess benzylamine (6a) and triethylamine were distilled off under reduced pressure. To the crude mass obtained was added water and extracted with dichloromethane. The dichloromethane layer was washed with water liberally. This isolated dichloromethane layer was treated with 5M HCl. The dichloromethane layer was again washed with water and the solvent was distilled off until a syrupy mass was obtained. This syrupy mass was added to n-heptane (8 volumes) under stirring. The solid product thus obtained was filtered off. This was dissolved in isopropanol (3 volumes) at 55° C. and then slowly cooled to 40° C. To this solution was added n-heptane (8 volumes) and the resulting mass was cooled under stirring to 10-15° C. The product obtained was filtered to get N-[6-(4-phenylbutoxy)hexyl]benzenemethanamine hydrochloride (8b). This was dried at 50-55° C.

Yield: 70% w/w
HPLC purity: 99.78%
Melting point: 135-140° C.
Appearance: light yellow solids Example 4

Preparation of 2-hydroxy-5-[[[6-(4-phenylbutoxy) hexylbenzyl]amino]acetyl]benzaldehyde (9a)

Intermediate (8b) was dissolved in dichloromethane (5 volumes) and stirred with an aqueous solution of sodium carbonate by maintaining pH ~8 at 25-30° C. for 30 minutes. The dichloromethane layer was separated and washed with water and the dichloromethane was distilled off to get an oily mass, the free base (7a) of intermediate (8b). The purified free base (7a) of intermediate (8b) (1.2 m/m) was dissolved in methyl ethyl ketone (5 volumes) in the presence of diisopropylethylamine (1.2 m/m) at 0-5° C. To this, intermediate (2a) dissolved in methyl ethyl ketone was added over 90 minutes at 0-5° C. The reaction mixture was stirred at 5-10° C. for 10 hours. Then the reaction mixture was quenched with water (20 volumes) and intermediate (9a) thus formed was extracted with n-heptane (3×10 volumes) at 20-30° C. The n-heptane layer was separated and passed through a Celite® bed to separate the polymeric mass. The n-heptane layer as such was used for further conversion.

Yield: Quantitative
HPLC purity: 98.50%

Example 5

Preparation of 4-hydroxy-α'-[[[6-(4-phenylbutoxy) hexyl]benzylamino]methyl]-1,3-benzenedimethanol (10a)

To the n-heptane layer containing intermediate (9a) obtained from example 4 was added methanol (10 volumes) and the biphasic mixture was cooled under stirring to −10° C. To this, sodium borohydride (7 m/m) was added in lots maintaining the temperature between 0-10° C. After complete addition, the reaction was maintained until disappearance of intermediate (9a) at 25-30° C. The reaction was carried out until a single peak of the completely reduced product (10a) was obtained. If required, a further 2-3 m/m sodium borohydride was added. After the reaction was over, the methanol layer was separated and the solvent was distilled off under reduced pressure. To the syrupy mass obtained was added water (20 volumes), ethyl acetate and dilute HCl (3M) under stirring. The reaction mass was stirred at 25-30° C. for an hour maintaining the pH between 2-3. Then to the reaction mass was added ethyl acetate (10 volumes) and the reaction mass was made basic (pH9) using sodium bicarbonate solution and extracted in ethyl acetate. The ethyl acetate layer was washed with water and the solvent was distilled off to obtain intermediate (10a) as a gummy mass.

Yield: 83% w/w
HPLC purity: 96.00%

Example 6

Preparation of 4-hydroxy-α'-[[[6-(4-phenylbutoxy) hexyl]amino]methyl]-1,3-benzenedimethanol (salmeterol) (11)

Intermediate (10a) obtained from the previous step (example 5) was taken in methanol (10 volumes). This solution was subjected to catalytic hydrogenolysis (20% Pd/C (20% w/w)) at ambient temperature and at atmospheric pressure. Hydrogen gas was purged at the rate of 2-3 kg/cm$^2$ at a temperature of 25-30° C. The reaction was monitored on HPLC until the disappearance of starting material (10a). After the reaction was over, the reaction mass was filtered through a Celite® bed to isolate the catalyst. The mother liquor obtained was distilled off. The residue obtained was swapped with ethyl acetate (3×8 volumes) and the resulting mass was stirred at 5-10° C. in ethyl acetate (8 volumes) for precipitation of salmeterol (11). The slurry was filtered to obtain a crude mass. This crude mass was again dissolved in methanol and subjected to activated carbon treatment at 25-30° C. Methanol was distilled off completely, followed by swapping with ethyl acetate (2×8 volumes). To the gummy mass obtained after swapping, ethyl acetate (8 volumes) was added and the mass was cooled at 5-10° C. under stirring. After 2 hours of stirring, the slurry was filtered off and solids (11) obtained were dried under reduced pressure at 40° C. to constant weight.

Yield: 20% w/w
HPLC purity: 98.00%

Example 7

Preparation of 4-hydroxy-α'-[[[6-(4-phenylbutoxy)hexyl]amino]methyl]-1,3-benzenedimethanol 1-hydroxy-2-naphthoate (salmeterol xinafoate) (12a)

To a solution of salmeterol (11) in methanol (5 volumes) was added an equimolar methanolic solution of 1-hydroxy-2-naphthoic acid at 25-30° C. The xinafoate salt (12a) immediately precipitated out. The slurry obtained was stirred further at 10-20° C. for 3 hours and the crude salmeterol xinafoate (12a) was isolated.

Yield: 116% w/w
HPLC purity: 99.50%

In order to prepare salmeterol xinafoate having an HPLC purity more than 99.8%, the above material was further purified by crystallization from methanol.

Yield: 75% w/w

The invention claimed is:

1. A process of preparing an ether (5), comprising the step of:
   (a) reacting 4-phenyl-1-butanol (3) and X—(CH$_2$)$_6$—X (4) in the presence of a phase transfer agent and NaI to obtain ether (5), wherein X are independently leaving groups:

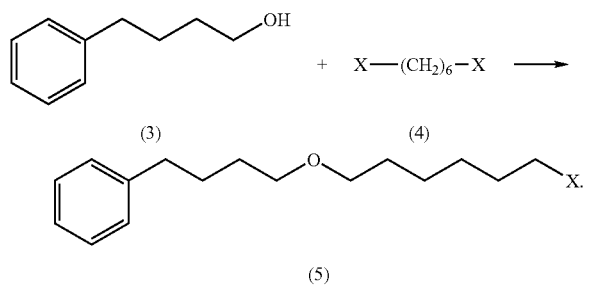

2. The process as claimed in claim 1, wherein:
   (a) X are independently —Cl, —Br, —I, —OTs, —OMs or —OTf; and/or
   (b) X—(CH$_2$)$_6$—X (4) is Br—(CH$_2$)$_6$—Br (4a).

3. The process as claimed in claim 1, wherein the reaction of step (a) takes place in the presence of:
   (a) a base; and/or
   (b) NaH.

4. The process as claimed in claim 1, wherein the phase transfer agent is Bu$_4$NBr.

5. The process as claimed in claim 1, wherein the reaction is carried out in:
   (a) an aprotic solvent; and/or
   (b) toluene, dimethylformamide, dimethyl sulfoxide, tetrahydrofuran, xylene, methyl t-butyl ether, diisopropyl ether, or a mixture thereof.

6. A process of preparing an amine (7) or a salt thereof, comprising the steps of:
   (a) carrying out step (a) as claimed in claim 1, and
   (b) reacting ether (5) and protected amine PgNH$_2$ (6) in the presence of a base to obtain amine (7) or a salt thereof, wherein Pg is a protecting group:

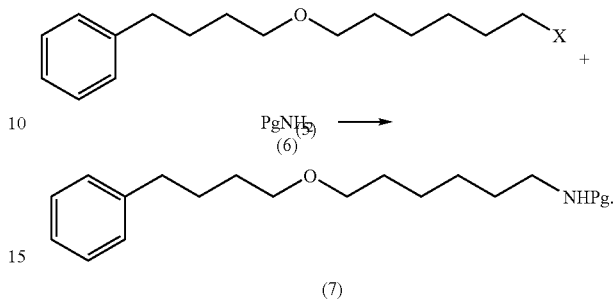

7. The process as claimed in claim 6, wherein the protected amine (6) used in step (b) is benzylamine.

8. The process as claimed in claim 6, wherein the base used in step (b) comprises triethylamine, potassium carbonate, sodium carbonate, pyridine, pyrrolidine, piperidine, diisopropylamine or diisopropylethylamine.

9. The process as claimed in claim 6, wherein the reaction of step (b) is carried out in the presence NaI.

10. The process as claimed in claim 6, wherein the reaction of step (b) is carried out in:
    (a) an organic solvent; and/or
    (b) acetonitrile, tetrahydrofuran, dimethylformamide, dimethylacetamide, methanol, ethanol, n-propanol, isopropanol, toluene, xylene, or a mixture thereof.

11. The process as claimed in claim 6, further comprising the steps of:
    (c) converting amine (7) into a salt (8) thereof, wherein X is an anion:

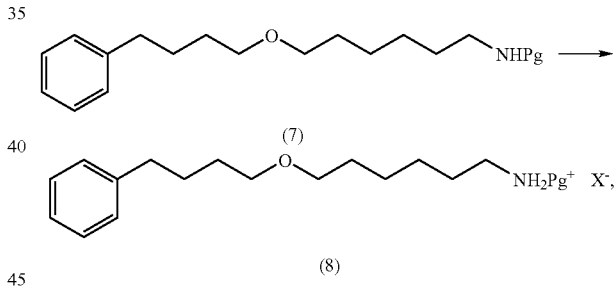

(d) purifying the salt (8), and
    (e) converting the purified salt (8) back into amine (7):

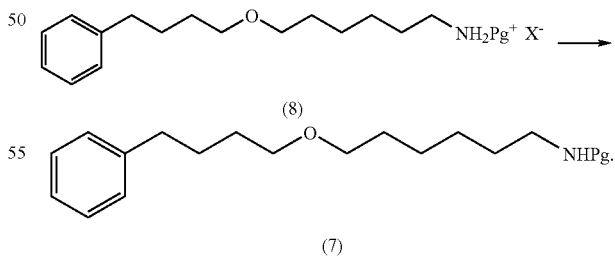

12. The process as claimed in claim 11, wherein the salt (8) is:
    (a) a hydrofluoride, hydrochloride, hydrobromide, hydroiodide, tartrate, formate, acetate, sulfate, hydrogen sulfate, nitrate, benzoate, maleate, fumarate, methanesulfonate, benzylsulfonate or citrate salt; and/or
    (b) a hydrochloride salt (8a):

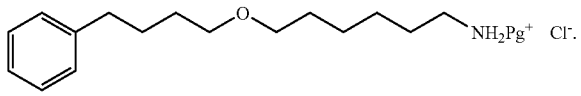

(8a)

13. The process as claimed in claim 11, wherein the conversion step (c) is carried out in:
   (a) a non-polar halogenated solvent in the presence of water; and/or
   (b) dichloromethane, dichloroethane, chloroform, or a mixture thereof, in the presence of water.

14. The process as claimed in claim 11, wherein the purification step (d) comprises:
   (a) washing the salt (8) with a non-polar solvent; and/or
   (b) washing the salt (8) with pentane, hexane, heptane, cyclohexane, diethyl ether, diisopropyl ether, t-butyl methyl ether, or a mixture thereof; and/or
   (c) recrystallising the salt (8) using a polar protic solvent and a non-polar aprotic solvent; and/or
   (d) recrystallising the salt (8) using a polar protic solvent and a non-polar aprotic solvent, wherein the polar protic solvent comprises methanol, ethanol, isopropanol, or a mixture thereof; and/or
   (e) recrystallising the salt (8) using a polar protic solvent and a non-polar aprotic solvent, wherein the non-polar aprotic solvent comprises pentane, hexane, heptane, toluene, or a mixture thereof; and/or
   (f) recrystallising the salt (8) using isopropanol and n-heptane.

15. The process as claimed in claim 11, wherein in step (e) the purified salt (8) is converted into amine (7) using:
   (a) a base; and/or
   (b) $Na_2CO_3$.

16. The process as claimed in claim 6 or 11, wherein the amine
   (7) or salt thereof is obtained:
   (a) more than 90% pure as measured by HPLC; and/or
   (b) in an overall yield of more than 50% by weight from 4-phenyl-1-butanol (3); and/or
   (c) on an industrial scale; and/or
   (d) in batches of 100 g or more.

17. The process as claimed in claim 6 or 11, wherein the process is carried out without purifying bromoether (5), amine (7) or salt (8) by chromatography or high vacuum distillation.

18. A process of preparing an aldehyde (9), comprising the steps of:
   (i) preparing an amine (7) or a salt thereof according to the process of claim 6 or 11; and
   (ii) reacting the amine (7) and an aldehyde (2) to obtain aldehyde (9), wherein X is a leaving group and Pg is a protecting group:

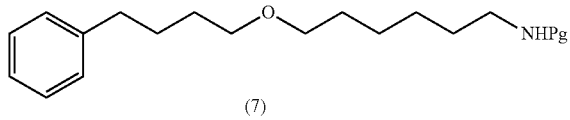

(7)

19. The process as claimed in claim 18, wherein step (ii) is carried out in the presence of:
   (a) a base; and/or
   (b) diisopropylethylamine.

20. The process as claimed in claim 18, wherein the reaction in step (ii) is carried out in:
   (a) an organic solvent; and/or
   (b) acetonitrile, methanol, ethanol, isopropanol, tetrahydrofuran, dimethylformamide, dimethyl sulfoxide, diethyl ether, diisopropyl ether, acetone, methyl ethyl ketone, or a mixture thereof.

21. The process as claimed in claim 18, wherein in step (ii) a solution of aldehyde (2) is added into a solution of amine (7).

22. The process as claimed in claim 18, wherein the reaction of step (ii) is carried out at a temperature of 0-15° C.

23. The process as claimed in claim 18, wherein in step (ii) the product aldehyde (9) is not isolated, but extracted into:
   (a) a non-polar solvent; and/or
   (b) pentane, hexane, heptane, cyclohexane, diethyl ether, diisopropyl ether, t-butyl methyl ether, or a mixture thereof.

24. The process as claimed in claim 18, wherein the aldehyde (2) is prepared by reacting 2-hydroxybenzaldehyde (1) with $XCH_2COX$ in the presence of $AlCl_3$:

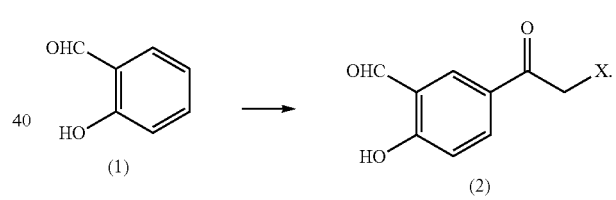

(1)        (2)

25. A process of preparing an alcohol (10), comprising the steps of:
   (iii) preparing an aldehyde (9) according to the process of claim 18; and

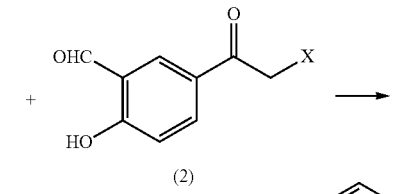

(2)

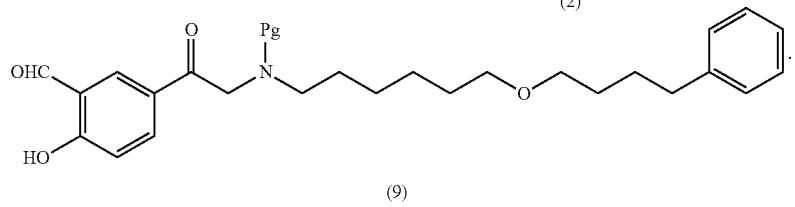

(9)

(iv) reducing aldehyde (9) to obtain alcohol (10):

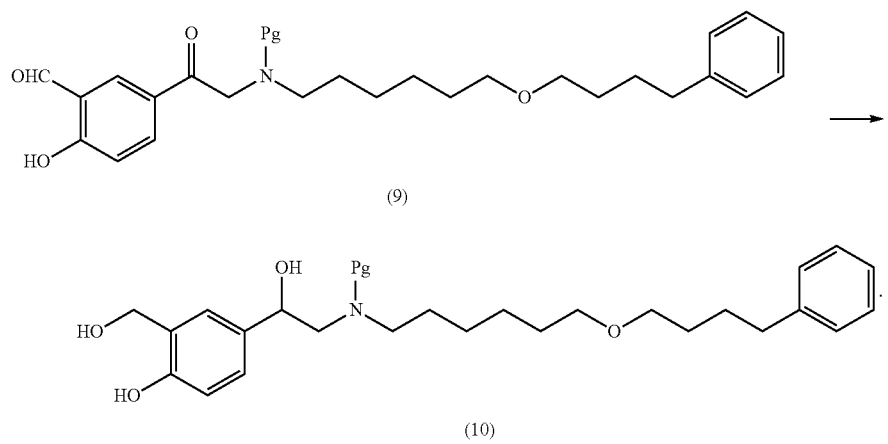

26. The process as claimed in claim 25, wherein the aldehyde (9) is prepared according to the process of claim 23 and the extracted solution comprising aldehyde (9) is used directly in step (iv).

27. The process as claimed in claim 25, wherein the reduction of step (iv) is carried out using:
   (a) NaBH$_4$; and/or
   (b) an excess of NaBH$_4$; and/or
   (c) the aldehyde (9) and NaBH$_4$ in a ratio of 1:4-10.

28. The process as claimed in claim 25, wherein the reduction of step (iv) is carried out in:
   (a) a biphasic solvent system; and/or
   (b) an organic biphasic solvent system; and/or
   (c) a $C_{1-3}$ alcohol and a $C_{5-7}$ hydrocarbon; and/or
   (d) a $C_{1-3}$ alcohol and a $C_{5-7}$ hydrocarbon, wherein the $C_{1-3}$ alcohol comprises methanol, ethanol, isopropanol, or a mixture thereof; and/or
   (e) a $C_{1-3}$ alcohol and a $C_{5-7}$ hydrocarbon, wherein the $C_{5-7}$ hydrocarbon comprises pentane, hexane, heptane, cyclohexane, or a mixture thereof.

29. A process of preparing salmeterol (11) or a salt thereof, comprising the steps of:
   (v) preparing an alcohol (10) according to the process of claim 25; and
   (vi) deprotecting alcohol (10) to obtain salmeterol (11):

30. The process as claimed in claim 29, wherein in step (vi) alcohol (10) is deprotected by:

(a) catalytic hydrogenolysis; and/or (b) catalytic hydrogenolysis, wherein Pd/C is used as the hydrogenation catalyst; and/or (c) catalytic hydrogenolysis, wherein the hydrogen gas is used at a pressure of 2-3 kg/cm$^2$.

31. The process as claimed in claim 29, wherein the reduction of step (iv) and the deprotection of step (vi) are carried out in the same reaction vessel.

32. The process as claimed in claim 29, wherein the salmeterol (11) is further converted into:

(a) a salt thereof; and/or

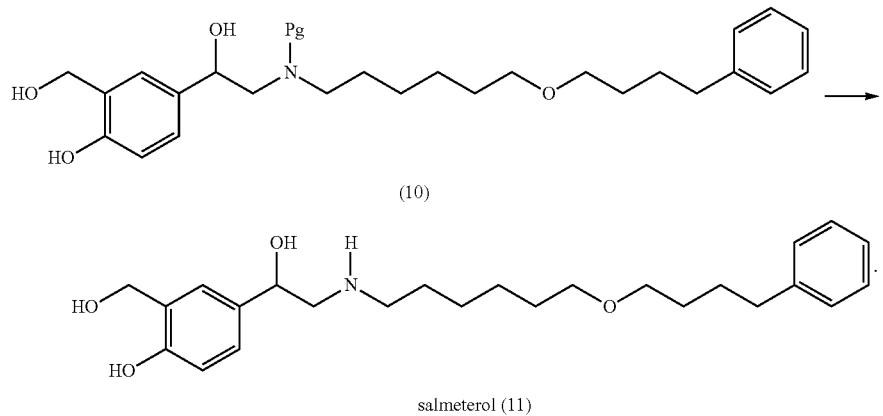

salmeterol (11)

(b) the xinafoate salt (12a):

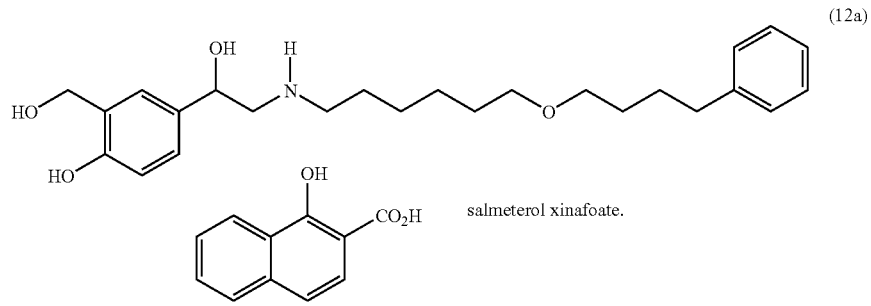 [SMILES: OCc1cc(C(O)CNCCCCCCOCCCCc2ccccc2)ccc1O ; O=C(O)c1ccc2ccccc2c1O]

33. The process as claimed in claim 29, wherein the salmeterol (11) or salt thereof is obtained:
    (a) more than 90% pure as measured by HPLC; and/or
    (b) in an overall yield of more than 12% by weight from amine (7); and/or
    (c) on an industrial scale; and/or
    (d) in batches of 150 g or more.

34. The process as claimed in claim 29, wherein the process is carried out without purifying aldehyde (9), alcohol (10), salmeterol (11) or salmeterol salt (12) by chromatography or high vacuum distillation.

35. A process of preparing an alcohol (10), comprising the step of:
    reducing aldehyde (9) to obtain alcohol (10) in a biphasic solvent system:

36. The process as claimed in claim 35, wherein the reduction of step (ii) is carried out using:
    (a) $NaBH_4$; and/or
    (b) an excess of $NaBH_4$; and/or
    (c) the aldehyde (9) and $NaBH_4$ in a ratio of 1:4-10.

37. The process as claimed in claim 35, wherein the reduction of step (ii) is carried out in:
    (a) an organic biphasic solvent system; and/or
    (b) a $C_{1-3}$ alcohol and a $C_{5-7}$ hydrocarbon; and/or
    (c) a $C_{1-3}$ alcohol and a $C_{5-7}$ hydrocarbon, wherein the $C_{1-3}$ alcohol comprises methanol, ethanol, isopropanol, or a mixture thereof; and/or
    (d) a $C_{1-3}$ alcohol and a $C_{5-7}$ hydrocarbon, wherein the $C_{5-7}$ hydrocarbon comprises pentane, hexane, heptane, cyclohexane, or a mixture thereof.

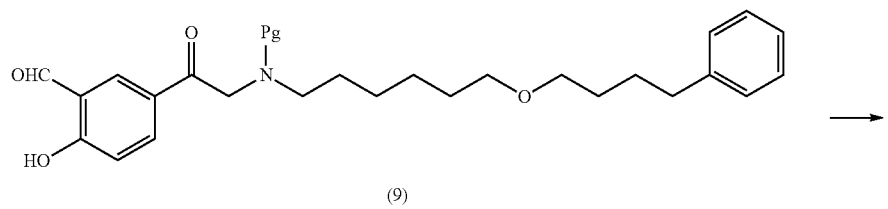

(9)

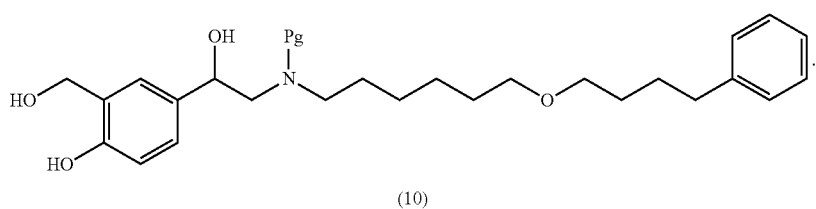

(10)

38. The process as claimed in claim 35, wherein the aldehyde (9) is prepared by the step:

(i) reacting an amine (7) and an aldehyde (2) to obtain the aldehyde (9), wherein X is a leaving group and Pg is a protecting group:

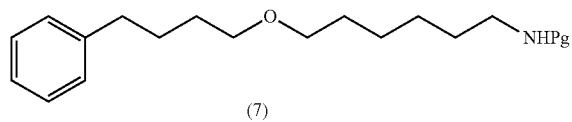

(7)

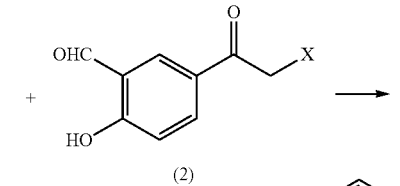

(2)

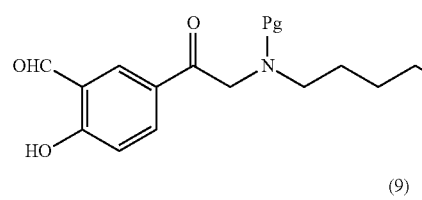

(9)

39. The process as claimed in claim 38, wherein step (i) is carried out in the presence of:
(a) a base; and/or
(b) diisopropylethylamine.

40. The process as claimed in claim 38, wherein the reaction in step (i) is carried out in:
(a) an organic solvent; and/or
(b) acetonitrile, methanol, ethanol, isopropanol, tetrahydrofuran, dimethylformamide, dimethyl sulfoxide, diethyl ether, diisopropyl ether, acetone, methyl ethyl ketone, or a mixture thereof.

41. The process as claimed in claim 38, wherein in step (i) a solution of aldehyde (2) is added into a solution of amine (7).

42. The process as claimed in claim 38, wherein the reaction of step (i) is carried out at a temperature of 0-15° C.

43. The process as claimed in claim 38, wherein in step (i) the product aldehyde (9) is not isolated, but extracted into:
(a) a non-polar solvent; and/or
(b) pentane, hexane, heptane, cyclohexane, diethyl ether, diisopropyl ether, t-butyl methyl ether, or a mixture thereof.

44. The process as claimed in claim 43, wherein the extracted solution comprising aldehyde (9) is used directly in step (ii).

45. The process as claimed in claim 38, wherein the amine (7) used in step (i) is prepared using a process as claimed in claim 6 or 11.

46. The process as claimed in claim 38, wherein the aldehyde (2) is prepared by reacting 2-hydroxybenzaldehyde (1) with $XCH_2COX$ in the presence of $AlCl_3$:

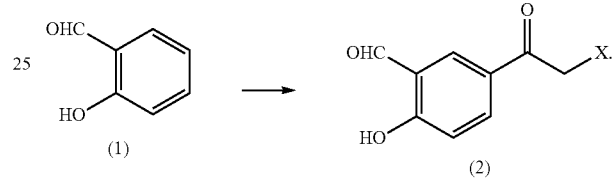

47. A process of preparing salmeterol (11) or a salt thereof, comprising the steps of:

(iii) preparing an alcohol (10) according to the process of claim 35; and (iv) deprotecting alcohol (10) to obtain salmeterol (11):

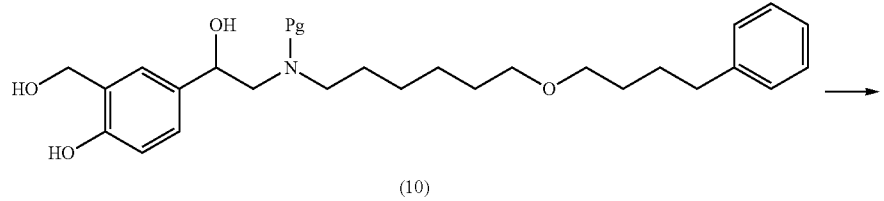

(10)

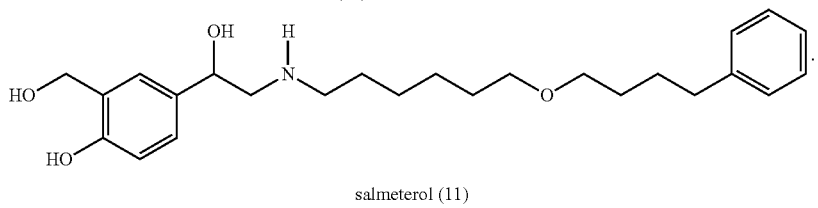

salmeterol (11)

48. The process as claimed in claim 47, wherein in step (iv) alcohol (10) is deprotected by:
(a) catalytic hydrogenolysis; and/or
(b) catalytic hydrogenolysis, wherein Pd/C is used as the hydrogenation catalyst; and/or
(c) catalytic hydrogenolysis, wherein the hydrogen gas is used at a pressure of 2-3 kg/cm$^2$.

49. The process as claimed in claim 47, wherein the reduction of step (ii) and the deprotection of step (iv) are carried out in the same reaction vessel.

50. The process as claimed in claim 47, wherein the salmeterol (11) is further converted into:
(a) a salt thereof; and/or (b) the xinafoate salt (12a):

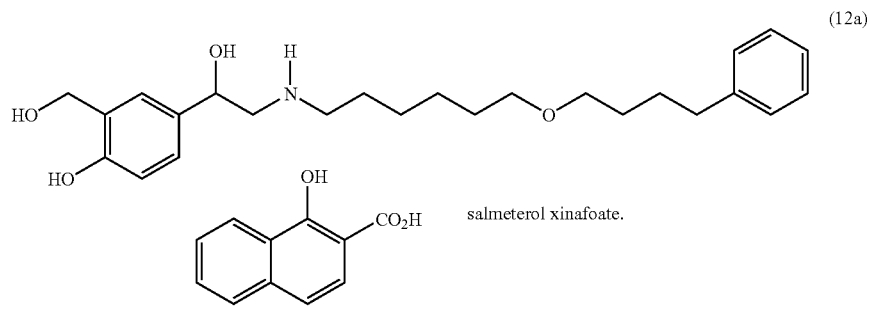 [SMILES: OCc1cc(C(O)CNCCCCCCOCCCCc2ccccc2)ccc1O ; O=C(O)c1ccc2ccccc2c1O]

salmeterol xinafoate.

51. The process as claimed in claim 47, wherein the salmeterol (11) or salt thereof is obtained:
(a) more than 90% pure as measured by HPLC; and/or
(b) in an overall yield of more than 12% by weight from amine (7); and/or
(c) on an industrial scale; and/or
(d) in batches of 150 g or more.

52. The process as claimed in claim 47, wherein the process is carried out without purifying aldehyde (9), alcohol (10), salmeterol (11) or salmeterol salt (12) by chromatography or high vacuum distillation.

* * * * *